United States Patent
Kang et al.

(10) Patent No.: US 12,383,217 B2
(45) Date of Patent: Aug. 12, 2025

(54) METHOD AND SYSTEM FOR SELECTING AN OPTIMAL FRAME USING DISTRIBUTION OF INTENSITY FOR EACH FRAME IMAGE OF MEDICAL IMAGING

(71) Applicant: Medipixel, Inc., Seoul (KR)

(72) Inventors: Min-Yeong Kang, Seoul (KR); Young Eon Kim, Seoul (KR)

(73) Assignee: Medipixel, Inc., Seoul (KR)

( * ) Notice: Subject to any disclaimer, the term of this patent is extended or adjusted under 35 U.S.C. 154(b) by 191 days.

(21) Appl. No.: 18/144,417

(22) Filed: May 8, 2023

(65) Prior Publication Data
US 2023/0355196 A1 Nov. 9, 2023

(30) Foreign Application Priority Data
May 9, 2022 (KR) .......................... 10-2022-0056641

(51) Int. Cl.
*A61B 6/50* (2024.01)
*A61B 6/00* (2024.01)
*G06T 7/00* (2017.01)

(52) U.S. Cl.
CPC ............. *A61B 6/504* (2013.01); *A61B 6/481* (2013.01); *G06T 7/0012* (2013.01); *G06T 2207/30101* (2013.01)

(58) Field of Classification Search
None
See application file for complete search history.

(56) References Cited

U.S. PATENT DOCUMENTS

| 5,533,085 A * | 7/1996 | Sheehan ................ A61B 6/481 378/95 |
| 2004/0102693 A1* | 5/2004 | Jenkins .................. A61B 6/481 600/410 |

(Continued)

FOREIGN PATENT DOCUMENTS

| JP | 2004174255 A | 6/2004 |
| KR | 10-2010-0060275 A | 6/2010 |
| KR | 10-20210101641 A | 8/2021 |

OTHER PUBLICATIONS

Bajaj, Retesh, et al. "A deep learning methodology for the automated detection of end-diastolic frames in intravascular ultrasound images." The International Journal of Cardiovascular Imaging 37 (2021): 1825-1837. (Year: 2021).*

(Continued)

*Primary Examiner* — Samah A Beg
(74) *Attorney, Agent, or Firm* — Banner & Witcoff, Ltd.

(57) ABSTRACT

Provided is a method for selecting an optimal frame using a distribution of intensities for each frame image of a medical image, which is performed by one or more processors of an information processing system. The method includes receiving a medical image associated with a blood vessel injected with a contrast agent, the medical image including a plurality of frame images, calculating an intensity for each of the plurality of frame images of the medical image, determining, based on a distribution of a plurality of intensities corresponding to the plurality of frame images, a frame section corresponding to a plurality of consecutive frame images of the plurality of frame images, and selecting, based on the determined frame section, a frame image from among the plurality of consecutive frame images.

12 Claims, 10 Drawing Sheets

(56) References Cited

U.S. PATENT DOCUMENTS

2011/0142288 A1* 6/2011 Diamant ............... G06T 7/0016
    382/128
2019/0380593 A1* 12/2019 Bouwman .............. A61B 6/465
2022/0164950 A1* 5/2022 Aben ..................... A61B 6/481

OTHER PUBLICATIONS

Ciusdel, Costin, et al. "Deep neural networks for ECG-free cardiac phase and end-diastolic frame detection on coronary angiographies." Computerized Medical Imaging and Graphics 84 (2020): 101749. (Year: 2020).*

Dehkordi, Maryam Taghizadeh. "Extraction of the best frames in coronary angiograms for diagnosis and analysis." Journal of Medical Signals & Sensors 6.3 (2016): 150-157. (Year: 2016).*

* cited by examiner

METHOD AND SYSTEM FOR SELECTING AN OPTIMAL FRAME USING DISTRIBUTION OF INTENSITY FOR EACH FRAME IMAGE OF MEDICAL IMAGING

CROSS-REFERENCE TO RELATED APPLICATION

This application claims priority to Korean Patent Application No. 10-2022-0056641, filed in the Korean Intellectual Property Office on May 9, 2022, the entire contents of which are hereby incorporated by reference.

BACKGROUND

Field

The present disclosure relates to a method and system for selecting an optimal frame using a distribution of intensities for each frame image of a medical image, and specifically, to a method and system for calculating intensity for each frame image, and determining a frame section where the intensity is stably maintained and selecting an optimal frame from the determined frame section.

Description of Related Art

Diagnosis, examination, and the like performed using medical images (e.g., X-ray, CT, MRI, and the like) often involve administering a contrast agent to the patient's body. The contrast agent increases the contrast in the image by artificially increasing the difference in X-ray absorbance, so that the blood vessel to be examined can be clearly distinguished from the surroundings. In a captured medical image, a blood vessel region filled with the contrast agent may appear darker (black) than the surrounding region.

Meanwhile, the medical image may include a plurality of frame images, and among these images, the medical staff can select an optimal frame image suitable for analysis of test results in which the target blood vessel and its surroundings are most clearly distinguished, that is, a frame image captured in a state in which the target blood vessel is evenly and sufficiently filled with the contrast agent, and analyze the selected optimal frame image to make a diagnosis, and the like.

According to a related method for selecting an optimal frame from among a plurality of frame images included in the medical image, among the plurality of frame images, a frame image having the highest intensity of the contrast agent may be selected to be an optimal frame. According to this related method, there is a problem in that an error frequently occurs in which a frame that is not suitable for analysis is selected to be an optimal frame. For example, a foreign material, not a contrast agent, is determined to be an intravascular contrast agent and so a frame at the moment when the foreign material is inserted is selected to be an optimal frame, or a frame captured in a state in which the contrast agent has flowed away so that there is almost no contrast agent remaining in some blood vessel regions and only some blood vessel regions are filled with the contrast agent, is selected to be an optimal frame.

SUMMARY

In order to solve one or more problems (e.g., the problems described above and/or other problems not explicitly described herein), the present disclosure provides a method for, a non-transitory computer-readable recording medium storing instructions for, and an apparatus (system) for selecting an optimal frame using a distribution of intensities for each frame image of a medical image.

The present disclosure may be implemented in a variety of ways, including a method, an apparatus (system), or a non-transitory computer-readable recording medium storing instructions.

A method may include receiving a medical image associated with a blood vessel injected with a contrast agent, the medical image including a plurality of frame images, calculating an intensity for each of the plurality of frame images of the medical image, determining, based on a distribution of a plurality of intensities corresponding to the plurality of frame images, a frame section corresponding to a plurality of consecutive frame images of the plurality of frame images, and selecting, based on the determined frame section, a frame image from among the plurality of consecutive frame images.

The calculating the intensity for each of the plurality of frame images of the medical image may include masking, using a machine learning model, a region determined to be the blood vessel in each of the plurality of frame images of the medical image, and calculating, based on the masked region, the intensity for a respective frame image of the plurality of frame images of the medical image.

The calculating the intensity for each of the plurality of frame images of the medical image may include calculating a reliability value for determining each of a plurality of pixels in each of the plurality of frame images of the medical image to be a blood vessel region, and calculating, based on the calculated reliability value, the intensity for each of the plurality of frame images of the medical image.

The determining the frame section may further include selecting, from among the plurality of frame images of the medical image, a plurality of consecutive frame images having intensities within a predefined threshold range, and determining, as the frame section, a frame section corresponding to the selected plurality of consecutive frame images.

The method may further include approximating the calculated intensity for each of the plurality of frame images with a continuous function, and calculating a local maximum value of the continuous function, wherein the predefined threshold range is defined based on the calculated local maximum value.

The determining the frame section may further include, as a criterion for determining the frame section, determining, based on a plurality of detected frame sections, a detected frame section having a largest local maximum value.

The determining the frame section may further include, based on a plurality of detected frame sections, determining, as the frame section, a detected frame section having a largest number of frame images, or a detected frame section having one of a largest maximum intensity value, a largest minimum intensity value, or a largest average intensity for frame images.

The selecting the frame image may include selecting, as the frame image, a frame image having a highest intensity in the frame section or a last frame image (e.g., a frame image corresponding to a last frame number in the frame section).

The method may include further include receiving electrocardiogram data measured when the medical image is captured, in which the selecting the frame image may include selecting a frame image corresponding to an end of diastole in the frame section using the electrocardiogram data.

The selected frame image may include a first region corresponding to the blood vessel; and a second region distinguishable from the first region.

There is provided a non-transitory computer-readable recording medium storing instructions for executing the method on a computer.

An information processing system is provided, which may include a memory, and one or more processors connected to the memory and configured to execute one or more computer-readable programs included in the memory, in which the one or more programs may further include instructions for receiving a medical image associated with a blood vessel injected with a contrast agent, the medical image including a plurality of frame images, calculating an intensity for each of the plurality of frame images of the medical image, determining, based on a distribution of a plurality of intensities corresponding to the plurality of frame images, a frame section corresponding to a plurality of consecutive frame images of the plurality of frame images, and selecting, based on the determined frame section, a frame image from among the plurality of consecutive frame images.

According to some examples of the present disclosure, an optimal frame may be objectively selected without requiring intervention of a user (e.g., a doctor), and the error of selecting a frame not suitable for analysis as an optimal frame can be prevented.

According to some examples of the present disclosure, by determining a frame section where the intensity of the contrast agent is stably maintained and selecting an optimal frame from the determined section, the error of selecting a frame not suitable for analysis as an optimal frame due to perturbation can be prevented. That is, the error sensitivity can be reduced.

The effects of the present disclosure are not limited to the effects described above, and other effects not described herein can be clearly understood by those of ordinary skill in the art (referred to as "ordinary technician") from the description including the claims.

BRIEF DESCRIPTION OF THE DRAWINGS

The above and other objects, features and advantages of the present disclosure will be described with reference to the accompanying drawings described below, where similar reference numerals indicate similar elements, but not limited thereto, in which.

DETAILED DESCRIPTION

Figure 1:
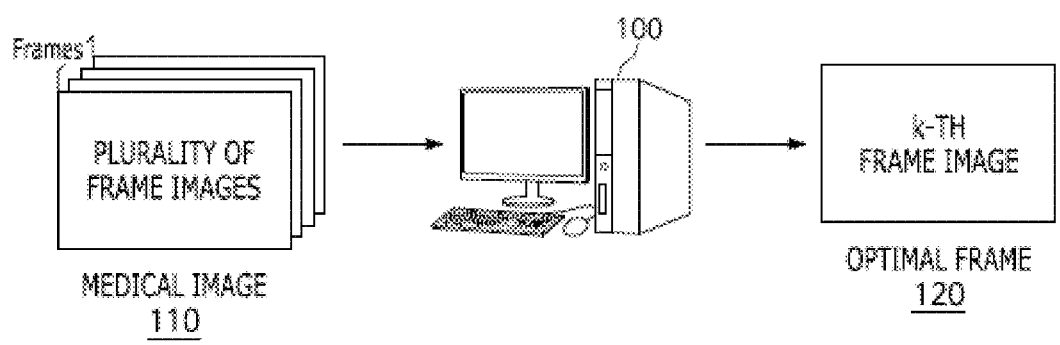
FIG. 1 is an exemplary configuration diagram illustrating an information processing system for selecting an optimal frame from a medical image.

Hereinafter, example details for the practice of the present disclosure will be described in detail with reference to the accompanying drawings. However, in the following description, detailed descriptions of well-known functions or configurations will be omitted if it may make the subject matter of the present disclosure rather unclear.

In the accompanying drawings, the same or corresponding components are assigned the same reference numerals. In addition, in the following description of various examples, duplicate descriptions of the same or corresponding components may be omitted. However, even if descriptions of elements are omitted, it is not intended that such elements are not included in any example.

Advantages and features of the disclosed examples and methods of accomplishing the same will be apparent by referring to examples described below in connection with the accompanying drawings. However, the present disclosure is not limited to the examples disclosed below, and may be implemented in various different forms, and the examples are merely provided to make the present disclosure complete, and to fully disclose the scope of the invention to those skilled in the art to which the present disclosure pertains.

The terms used herein will be briefly described prior to describing the disclosed example(s) in detail. The terms used herein have been selected as general terms which are widely used at present in consideration of the functions of the present disclosure, and this may be altered according to the intent of an operator skilled in the art, related practice, or introduction of new technology. In addition, in specific cases, certain terms may be arbitrarily selected by the applicant, and the meaning of the terms will be described in detail in a corresponding description of the example(s). Therefore, the terms used in the present disclosure should be defined based on the meaning of the terms and the overall content of the present disclosure rather than a simple name of each of the terms.

As used herein, the singular forms 'a,' 'an,' and 'the' are intended to include the plural forms as well, unless the context clearly indicates the singular forms. Further, the plural forms are intended to include the singular forms as well, unless the context clearly indicates the plural forms. Further, throughout the description, when a portion is stated as "comprising (including)" a component, it intends to mean that the portion may additionally comprise (or include or have) another component, rather than excluding the same, unless specified to the contrary.

Further, the term "module" or "unit" used herein refers to a software or hardware component, and "module" or "unit" performs certain roles. However, the meaning of the "module" or "unit" is not limited to software or hardware. The "module" or "unit" may be configured to be in an addressable storage medium or configured to play one or more processors. Accordingly, as an example, the "module" or "unit" may include components such as software components, object-oriented software components, class components, and task components, and at least one of processes, functions, attributes, procedures, subroutines, segments of program code, drivers, firmware, micro-codes, circuits, data, database, data structures, tables, arrays, or variables. Furthermore, functions provided in the components and the "modules" or "units" may be combined into a smaller number of components and "modules" or "units", or further divided into additional components and "modules" or "units."

According to an example of the present disclosure, the "module" or "unit" may be implemented as a processor and a memory. The "processor" should be interpreted broadly to encompass a general-purpose processor, a central processing unit (CPU), a graphic processing unit (GPU), a microprocessor, a digital signal processor (DSP), a controller, a microcontroller, a state machine, and so forth. Under some circumstances, the "processor" may refer to an application-specific integrated circuit (ASIC), a programmable logic device (PLD), a field-programmable gate array (FPGA), and so on. The "processor" may refer to a combination for processing devices, e.g., a combination of a DSP and a microprocessor, a combination of a plurality of microprocessors, a combination of one or more microprocessors in conjunction with a DSP core, or any other combination of such configurations. In addition, the "memory" should be interpreted broadly to encompass any electronic component that is capable of storing electronic information. The "memory" may refer to various types of processor-readable media such as random access memory (RAM), read-only memory (ROM), non-volatile random access memory (NVRAM), programmable read-only memory (PROM), erasable programmable read-only memory (EPROM), electrically erasable PROM (EEPROM), flash memory, magnetic or optical data storage, registers, and so on. The memory is said to be in electronic communication with a processor if the processor can read information from and/or write information to the memory. The memory integrated with the processor is in electronic communication with the processor.

In the present disclosure, a "system" may refer to at least one of a server device and a cloud device, but not limited thereto. For example, the system may include one or more server devices. In another example, the system may include one or more cloud devices. In yet another example, the system may include both the server device and the cloud device operated in conjunction with each other.

In the present disclosure, a "medical image" may refer to a picture and/or an image captured for diagnosis, treatment, and prevention of a disease, and may refer to a picture and/or an image captured inside/outside the patient's body. Examples of medical images may include pictures and/or images of all modalities, such as X-ray images, ultrasound images, Chest radiograph, Computed Tomography (CT), Positron emission tomography (PET), Magnetic Resonance Imaging (MRI), Sonography (Ultrasound, US), Functional Magnetic Resonance Imaging (fMRI), Digital pathology whole slide image (WSI), and Digital Breast Tomosynthesis (DBT). In some examples of the present disclosure, the "medical image" may refer to a plurality of frame images included in the medical image. In addition, in some examples of the present disclosure, the "medical image" may include a medical image obtained by capturing a blood vessel of a patient who has been administered the contrast agent.

In the present disclosure, the "frame image" may refer to a still image that forms the medical image. In some examples of the present disclosure, each of the plurality of frame images included in the medical image may be sequentially assigned a frame number (e.g., first frame image, second frame image, . . . , n-th frame image, and so on) according to the order in which the medical image was captured. In addition, in some examples of the present disclosure, the "frame image" may be referred to as the "image."

In the present disclosure, the "machine learning model" may include any model that is used to infer an answer to a given input. The machine learning model may include an artificial neural network model including an input layer, a plurality of hidden layers, and an output layer. In an example, each layer may include one or more nodes. In addition, the machine learning model may include weights associated with a plurality of nodes included in the machine learning model. In an example, the weights may include any parameter associated with the machine learning model. In the present disclosure, the machine learning model may refer to an artificial neural network model, and the artificial neural network model may refer to the machine learning model. The machine learning model herein may be a model trained with various learning methods. For example, various learning methods such as supervised learning, unsupervised learning, reinforcement learning, and the like may be used herein.

In the present disclosure, "learning" may refer to any process of changing weights associated with the machine learning model by using the training data and/or the ground-truth labels. The learning may refer to a process of changing or updating weights associated with the machine learning model through one or more of forward propagation and backward propagation of the machine learning model by using the training images and the ground-truth labels (e.g., masked regions or masked images).

In the present disclosure, "each of a plurality of A" may refer to each of all components included in the plurality of A, or may refer to each of some of the components included in a plurality of A. For example, each of a plurality of frame images may refer to each of all frame images included in the plurality of frame images, or to each of some frame images included in the plurality of frame images.

In the present disclosure, "similar" may encompass sameness and similarity. For example, when two pieces of information are similar, it may mean that the two pieces of information are the same as or similar to each other.

FIG. 1 illustrates an exemplary configuration of an information processing system 100 for selecting an optimal frame 120 from a medical image 110. The information processing system 100 may receive the medical image 110 and select the optimal frame 120 (e.g., the k-th frame image) from among a plurality of frame images (e.g., the first frame image, the second frame image, . . . , the n-th frame image, and so on) included in the received medical image 110. While the information processing system 100 is illustrated as one computing device in FIG. 1, aspects are not limited thereto, and the information processing system 100 may be configured to process information and/or data in a distributed manner through a plurality of computing devices. The information processing system 100 may be any computing device that is used to select the optimal frame 120 from the medical image 110. In an example, the computing device may refer to any type of device equipped with a computing function, and may be a notebook, a desktop, a laptop, a server, a cloud system, and the like, for example, but is not limited thereto.

Although a storage system capable of communicating with the information processing system 100 is not illustrated in FIG. 1, the information processing system 100 may be connected to or configured in communication with one or more storage systems. The storage system connected to or configured in communication with the information processing system 100 may be a device or cloud system that stores and manages various data associated with the task of selecting optimal frame. For efficient data management, the storage system may store and manage various types of data using a database. In this case, the various types of data may include any data related to selecting an optimal frame, and for example, the various types of data may include machine learning models, training data, medical images, electrocardiogram data, and the like, but are not limited thereto.

The information processing system 100 may receive the medical image 110 obtained by capturing blood vessels of the patient who has been administered the contrast agent. Such medical images 110 may be received through a storage medium (e.g., a hospital system, a local/cloud storage system, and the like) capable of communication. The information processing system 100 may select the optimal frame 120 from among a plurality of frame images included in the received medical image 110. In this example, the optimal frame 120 may refer to a frame image of a plurality of frame images included in the medical image 110, that is most suitable for analysis for diagnosis, treatment, prevention, and the like of a disease. For example, the optimal frame 120 may include a frame that is captured in a state in which the target blood vessel region is sufficiently and evenly filled with the contrast agent, thus providing a clear distinction between a region corresponding to the blood vessel and a region not corresponding to the blood vessel in the image. The information processing system 100 may calculate an intensity for each of a plurality of frame images included in the medical image 110, determine a frame section for which a high intensity is calculated consistently and stably, and select one frame from the determined frame section, thereby selecting the optimal frame 120. Accordingly, the optimal frame 120 can be objectively selected without requiring intervention of a user (e.g., a doctor), and the error of selecting a frame not suitable for analysis as the optimal frame 120 can be prevented.

Figure 2:
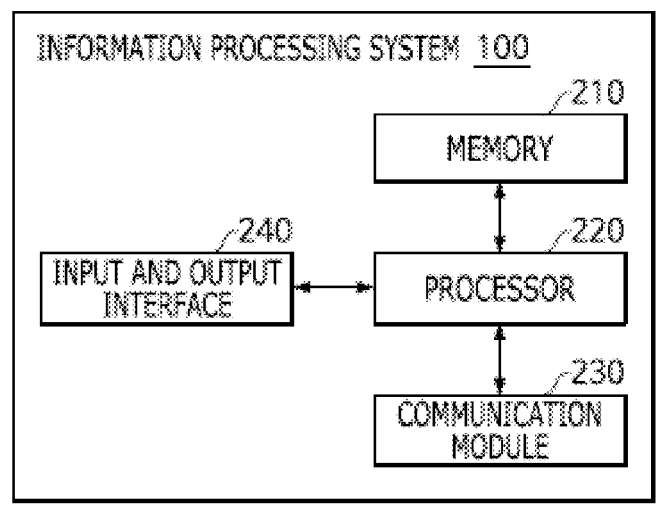
FIG. 2 is a block diagram illustrating an internal configuration of an information processing system.

FIG. 2 is a block diagram illustrating an internal configuration of the information processing system 100. The information processing system 100 may include a memory 210, a processor 220, a communication module 230, and an input and output interface 240. As illustrated in FIG. 2, the information processing system 100 may be configured to communicate information and/or data through a network by using the communication module 230. The information processing system 100 may be configured with at least one device including the memory 210, the processor 220, the communication module 230, and the input and output interface 240.

The memory 210 may include any non-transitory computer-readable recording medium. The memory 210 may include a permanent mass storage device such as read only memory (ROM), disk drive, solid state drive (SSD), flash memory, and so on. In another example, a non-destructive mass storage device such as ROM, SSD, flash memory, disk drive, and so on may be included in the information processing system 100 as a separate permanent storage device that is distinct from the memory 210. In addition, the memory 210 may store an operating system and at least one program code (e.g., a code installed and driven in the information processing system 100 to select optimal frame, or the like).

These software components may be loaded from a computer-readable recording medium separate from the memory 210. Such a separate computer-readable recording medium may include a recording medium directly connectable to the information processing system 100, and may include a computer-readable recording medium such as a floppy drive, a disk, a tape, a DVD/CD-ROM drive, a memory card, and the like, for example. In another example, the software components may be loaded into the memory 210 through the communication module 230 rather than the computer-readable recording medium. For example, at least one program may be loaded into the memory 210 based on a computer program (e.g., a program or the like for selecting an optimal frame, or the like) installed by the files provided by the developers or by a file distribution system that distributes an installation file of an application through the communication module 230.

The processor 220 may be configured to process the commands of the computer program by performing basic arithmetic, logic, and input and output computations. The commands may be provided to a user terminal (not illustrated) or another external system by the memory 210 or the communication module 230. For example, the processor 220 may receive a medical image, calculate an intensity for each of a plurality of frame images included in the medical image, determine a frame section corresponding to a plurality of consecutive frame images based on a distribution of a plurality of intensities corresponding to the plurality of frame images, and select one frame image from among the plurality of consecutive frame images corresponding to the frame section, thereby selecting an optimal frame.

The communication module 230 may provide a configuration or function for the user terminal (not illustrated) and the information processing system 100 to communicate with each other through a network, and may provide a configuration or function for the information processing system 100 to communicate with an external system (e.g., a separate cloud system). For example, control signals, commands, data, and the like provided under the control of the processor 220 of the information processing system 100 may be transmitted to the user terminal and/or the external system through the communication module 230 and the network through the communication module of the user terminal and/or an external system. For example, the optimal frame selected by the information processing system 100 may be transmitted to the user terminal and/or the external system through the communication module 230 and the network through the communication module of the user terminal and/or an external system. In addition, the user terminal and/or the external system that received the optimal frame may output the received information through a device capable of outputting a display.

In addition, the input and output interface 240 of the information processing system 100 may be a means for interfacing with a device (not illustrated) for inputting or outputting, which may be connected to the information processing system 100 or included in the information processing system 100. In FIG. 2, the input and output interface 240 is illustrated as a component configured separately from the processor 220, but aspects are not limited thereto, and the input and output interface 240 may be configured to be included in the processor 220. The information processing system 100 may include more components than those illustrated in FIG. 2. Meanwhile, most of the related components may not necessarily require exact illustration.

The processor 220 of the information processing system 100 may be configured to manage, process, and/or store the information and/or data received from a plurality of user terminals and/or a plurality of external systems. The processor 220 may receive the medical image from the user terminal and/or the external system. The processor 220 may calculate an intensity for each of a plurality of frame images included in the medical image, determine a frame section corresponding to a plurality of consecutive frame images based on a distribution of a plurality of intensities corresponding to the plurality of frame images, select one frame image from among the plurality of consecutive frame images corresponding to the frame section, thereby selecting an optimal frame, and output the selected optimal frame through the device capable of outputting a display, which is connected to the information processing system 100.

Figure 3:
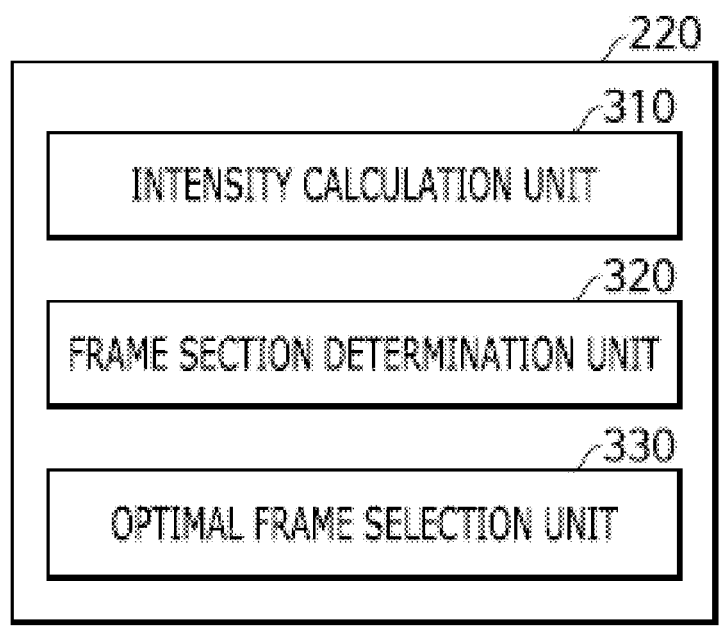
FIG. 3 is a diagram illustrating an internal configuration of a processor of the information processing system.

FIG. 3 is a diagram illustrating an internal configuration of the processor 220 of the information processing system. The processor 220 may include an intensity calculation unit 310, a frame section determination unit 320, and an optimal frame selection unit 330. Although the internal components of the processor 220 are divided by functions and described in FIG. 3, this does not necessarily mean that they are physically separated. In addition, the internal configuration of the processor 220 illustrated in FIG. 3 is only an example, and it is not intended to depict essential configurations only. Accordingly, in some examples, the processor 220 may be implemented differently, such as by adding components other than those internal components illustrated, or by omitting some of the illustrated components.

The processor 220 may receive a medical image obtained by capturing blood vessels of the patient who has been administered the contrast agent. In this case, the medical image may sequentially include a plurality of frame images in order of time the frame images are captured. The processor 220 may further receive electrocardiogram data of the patient that was measured at the same time as when the medical image was captured. Such medical images and/or electrocardiogram data may be received from a storage system (e.g., hospital system, electronic medical records, prescription delivery system, medical imaging system, examination information system, other local/cloud storage systems, and the like) connected to or in communication with the information processing system, an internal memory, and/or a user terminal. The received medical image and/or electrocardiogram data may be provided to the intensity calculation unit 310, the frame section determination unit 320, and/or the optimal frame selection unit 330 and used to select an optimal frame of the medical image.

The intensity calculation unit 310 may calculate an intensity for each of a plurality of frame images of the medical image. In this case, the intensity for the frame image may refer to the intensity of the contrast agent which can be calculated from the frame image. For example, the intensity for the frame image may be a numerical value reflecting the degree that the region corresponding to the blood vessel filled with the contrast agent is distinguished from the rest of the region in the frame image. The intensity for the frame image may be calculated with various methods.

The intensity calculation unit 310 may mask a region determined to be the blood vessel in each of a plurality of frame images of the medical image by using the machine learning model, and calculate the intensity for each of the frame images of the medical image based on the masked region. This will be described below in detail with reference to FIG. 4.

According to another example, the intensity calculation unit 310 may calculate reliability values for determining each of a plurality of pixels in each of a plurality of frame images of the medical image to be the blood vessel region, and calculate the intensity for each of the plurality of frame images of the medical image based on the calculated reliability values. This will be described below in detail with reference to FIG. 5. The method for calculating the intensity for the frame image described above is merely an example, and the scope of the present disclosure is not limited thereto. Accordingly, any intensity calculation method including intensity calculation method and the like using various filters, kernels, or models not described herein may be applied.

The frame section determination unit 320 may determine a consecutive frame section for which a high intensity is calculated stably, based on the distribution of intensities for each of the plurality of frame images calculated by the intensity calculation unit 310.

The frame section determination unit 320 may select, from among a plurality of frame images of the medical image, a plurality of consecutive frame images having intensities for the frame images within a predefined threshold range, and detect a frame section corresponding to the selected plurality of consecutive frame images. For example, the frame section determination unit 320 may approximate the calculated intensity for each of the plurality of frame images with a continuous function, and calculate a maximum value of the approximated continuous function. The frame section determination unit 320 may select a plurality of consecutive frame images included in a threshold range defined based on the calculated maximum value and detect a frame section corresponding to the selected plurality of consecutive frame images. This will be described below in detail with reference to FIG. 6.

If a plurality of frame sections are detected in the process of detecting the frame section, the frame section determination unit 320 may determine one of the detected sections to be the final frame section. For example, the frame section determination unit 320 may determine a frame section to be the final frame section if the frame section has the largest maximum value that serves as a criterion for detecting the frame section. As another example, the frame section determination unit 320 may determine a frame section to be the final frame section if the frame section has the largest number of frame images corresponding to the frame section. As yet another example, the frame section determination unit 320 may determine a frame section to be the final frame section if the frame section has one of the largest maximum intensity value, the largest minimum intensity value, or the largest average intensity for the frame images corresponding to the frame section. A method for determining one final frame section when a plurality of frame sections are detected will be described below in detail with reference to FIG. 7.

The frame section determination unit 320 may determine the final frame section with a frame section for which the high intensity is calculated continuously and stably, and not a frame section for which the high intensity is calculated as an instantaneous peak value, using not only the method described above, but also various other methods. Since the process of filling the blood vessels with the contrast agent is a continuous process, it can be estimated that the frame images captured while the entire blood vessel is filled with the contrast agent evenly (that is, in a state in which the blood vessel region and other regions are most clearly distinguished and suitable for analysis) would be present in the frame section for which the high intensity of the contrast agent is calculated consistently and stably. Therefore, by determining a frame section for which the high intensity is calculated consistently and stably, and selecting an optimal frame from the determined frame section, it is possible to select an optimal frame in which the blood vessel region and other regions are most clearly distinguished.

The optimal frame selection unit 330 may select one frame image from among a plurality of consecutive frame images corresponding to the frame section determined by the frame section determination unit 320. For example, the optimal frame selection unit 330 may select a frame image having the highest intensity in the frame section to be an optimal frame. As another example, the optimal frame selection unit 330 may select a frame image corresponding to the last frame in the frame section to be an optimal frame. As yet another example, the optimal frame selection unit 330 may select a frame corresponding to the end of diastole within a frame section using the received electrocardiogram data and extract a frame image corresponding to the selected frame so as to select an optimal frame. A method for the optimal frame selection unit 330 to select an optimal frame from the determined frame section will be described below in detail with reference to FIG. 8.

Figure 4:
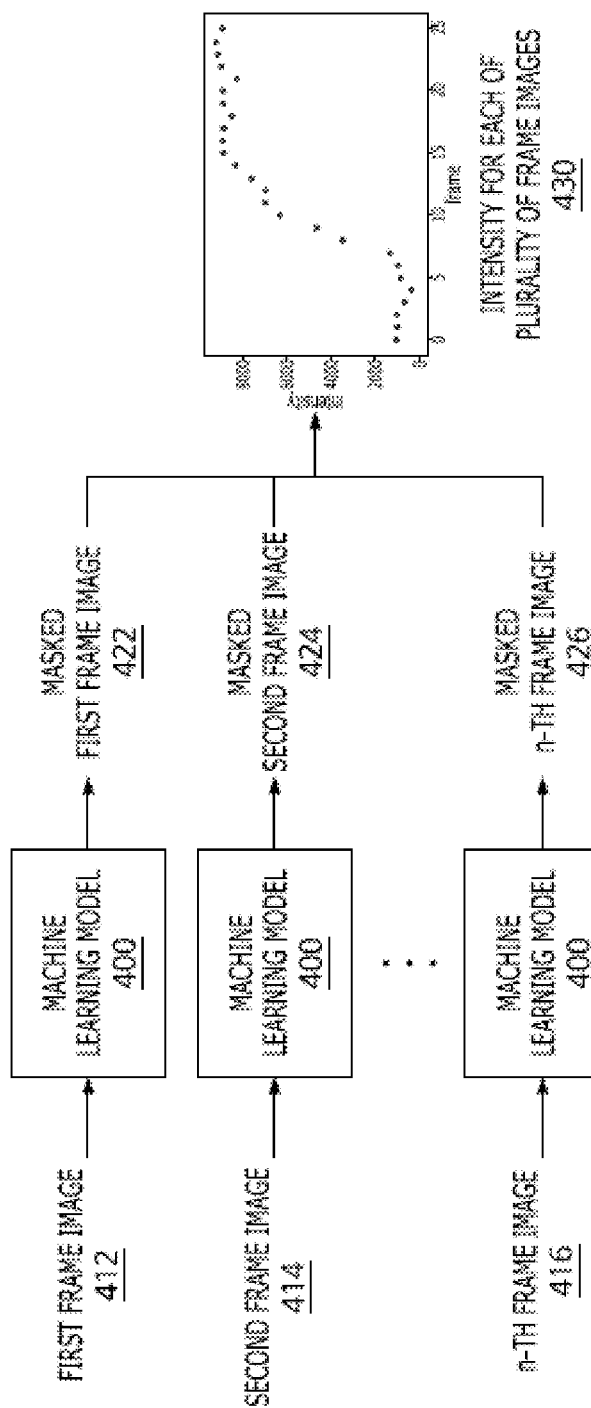
FIG. 4 is a diagram illustrating an example of calculating an intensity for each of a plurality of frame images of a medical image.

FIG. 4 is a diagram illustrating an example of calculating an intensity 430 for each of a plurality of frame images of a medical image. The intensity for the frame image may refer to the intensity of the contrast agent that can be calculated from the frame image. For example, the intensity for the frame image may be a numerical value reflecting the degree that the region corresponding to the blood vessel injected with the contrast agent is distinguished from the rest of the region in the frame image. The intensity for the frame image may be calculated with various methods.

The information processing system may mask a region determined to be the blood vessel (e.g., a region determined to have been injected with the contrast agent) in each of the plurality of frame images 412, 414, and 416 included in the medical image by using a machine learning model 400, and calculate the intensity 430 for each of the frame images of the medical image based on the masked region.

Specifically, first, the information processing system may input each of the plurality of frame images 412, 414, and 416 to the machine learning model 400, and acquire a plurality of frame images 422, 424, and 426 in which regions determined to be the blood vessels are masked. The machine learning model 400 may be a model trained to perform a masking process on a region determined to be the blood vessel in the input image and output the masked image. For example, the machine learning model 400 may be a model trained by supervised learning with the training data including pairs of a plurality of training images and images (ground-truth labels) in which regions corresponding to blood vessels (e.g., regions injected with contrast agent) in each training image are masked, but is not limited thereto. In addition, a semantic segmentation-based machine learning model may be used to classify a region determined to be the blood vessel in the input image, but aspects are not limited thereto, and any type of machine learning model may be used.

The information processing system may calculate the intensity 430 for each of the plurality of frame images based on the plurality of masked frame images 422, 424, and 426. For example, the information processing system may calculate the number of pixels of the masked region in each of the plurality of masked frame images 422, 424, and 426 so as to calculate the intensity for each of the frame images 422, 424, and 426. In this case, the region masked by the machine learning model 400 may be assumed to be the region injected with the contrast agent. As a specific example, if the number of pixels of the masked region in the masked first frame image 422 is 1000, the intensity for the first frame image may be calculated as 1000, and if the number of pixels of the masked region in the masked n-th frame image 426 is 8500, the intensity for the n-th frame image may be calculated as 8500. In a similar manner, the information processing system may calculate the intensity 430 for each of the plurality of frame images.

Figure 5:
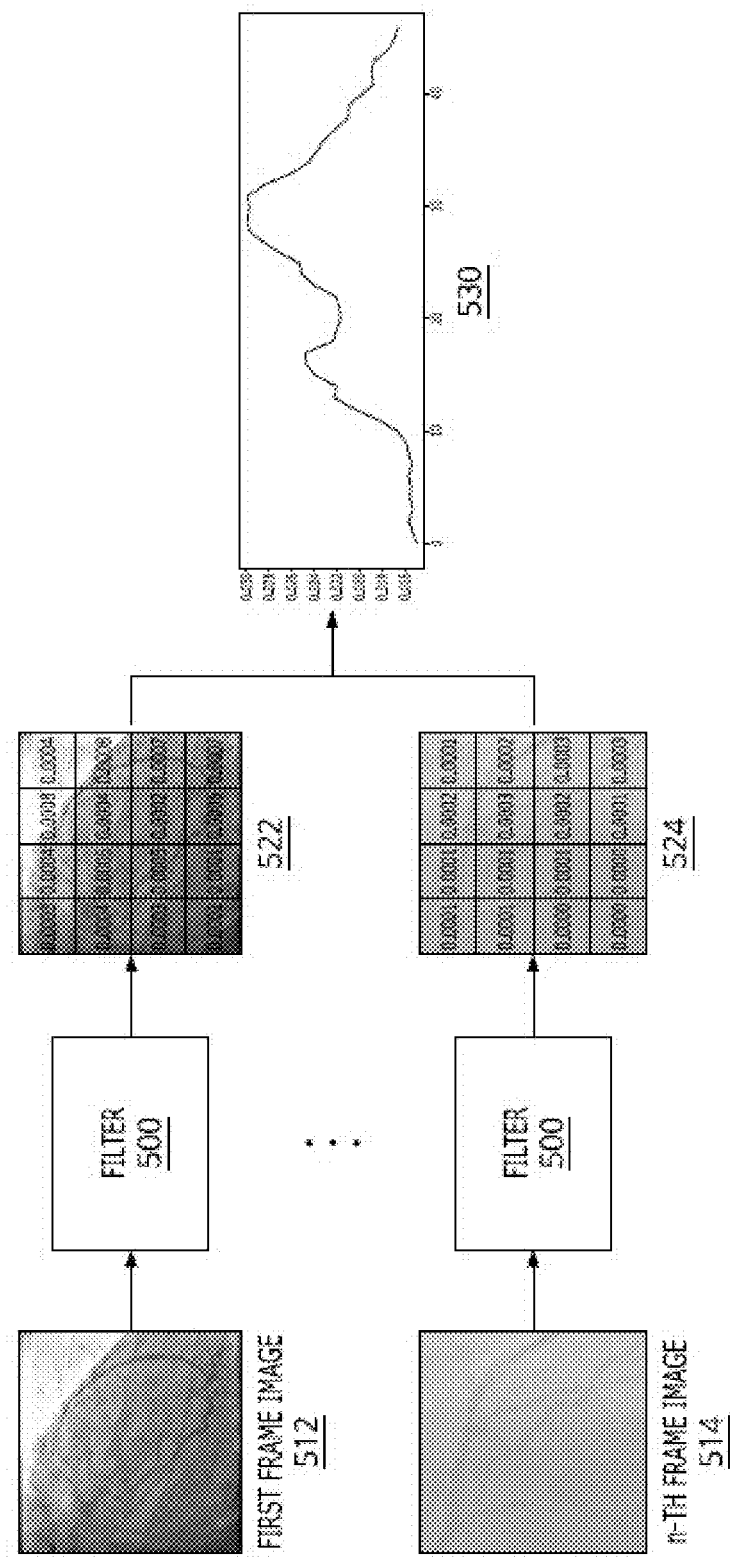
FIG. 5 is a diagram illustrating an example of calculating an intensity for each of a plurality of frame images of a medical image.

FIG. 5 is a diagram illustrating an example of calculating an intensity 530 for each of a plurality of frame images of a medical image. The information processing system may calculate reliability values 522 and 524 for determining each of a plurality of pixels in each of a plurality of frame images 512 and 514 of the medical image to be the blood vessel region, and calculate the intensity 530 for each of a plurality of frame images of the medical image based on the calculated reliability values 522 and 524.

For example, the information processing system may use a filter 500 to acquire the reliability values 522 and 524 for determining each of a plurality of pixels included in each of the plurality of frame images 512 and 514 to be the blood vessel region. In this case, the filter 500 may be a filter that outputs a reliability value for each of a plurality of pixels included in the input image that are determined to correspond to a vessel-like or tube-like structure, and may include a Frangi filter, for example, but is not limited thereto.

A specific example is shown in FIG. 5. FIG. 5 illustrates an example based on the assumption that each of the frame images 512 and 514 includes 16 pixels for convenience of description. As shown, the information processing system may input the first frame image 512 to the filter 500 to acquire the reliability value 522 for determining each of 16 pixels included in the first frame image to be the blood vessel region, and input the n-th frame image 514 to the filter 500 to acquire the reliability value 524 for determining each of 16 pixels included in the n-th frame image to be the blood vessel region. In this way, the information processing system may acquire the reliability values 522 and 524 for determining each of a plurality of pixels included in each of the plurality of frame images 512 and 514 included in the medical image to be the blood vessel region. The information processing system may scale the reliability values such that the reliability values 522 and 524 calculated for the entire medical image have a value between 0 and 1. If the size is adjusted, the reliability value in the following description of FIG. 5 may refer to the scaled reliability value. The information processing system may calculate, as the intensity 530 for each of the frame images, a value obtained by summing, for each frame image, the reliability values 522 and 524 for determining each of the plurality of pixels to be the blood vessel region. For example, a value obtained by summing all reliability values 522 for determining each of the 16 pixels included in the first frame image to be the blood vessel region may be calculated as the intensity for the first frame image, and in this way, the intensity 530 for each of the plurality of frame images included in the medical image may be calculated.

The method for calculating the intensity for the frame image described above with reference to FIGS. 5 to 6 is merely an example, and the scope of the present disclosure is not limited thereto. Accordingly, any intensity calculation method including intensity calculation methods using various filters, kernels, or models not described herein may also be applied.

Figure 6:
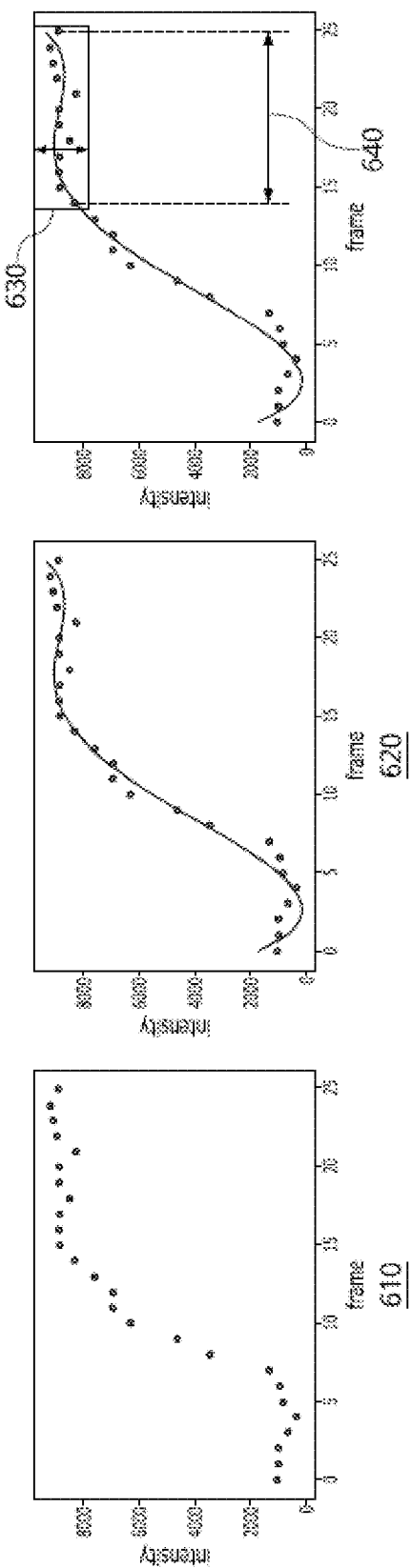
FIG. 6 is a diagram illustrating an example of a method for detecting a frame section.

FIG. 6 is a diagram illustrating an example of a method for detecting a frame section 640. The information processing system may detect the frame section 640 with the stably maintained intensities based on a distribution 610 of intensities for the frame image. Since the process of filling the blood vessels with the contrast agent is a continuous process, after the contrast agent is administered to the patient, the contrast agent may be gradually and continuously filled in the blood vessels of the target region, maintained in the state of being evenly filled in the vessels to some extent, and gradually and continuously withdrawn. Accordingly, it can be estimated that a frame image captured while the contrast agent is evenly and sufficiently filled in the blood vessels of the target region would be present in a frame section where the intensity of the contrast agent is stably maintained. Even when a high intensity of the contrast agent is calculated, if the intensity is not on the gradual and continuous increase and the high intensity is calculated by an instantaneous peak, it is highly likely that the contrast agent is not evenly filled or the result is affected by other external factors. Accordingly, the information processing system may determine the frame section 640 where the intensity is increased continuously and gradually and maintained stably, and select a frame image from the determined frame section 640, thereby selecting an optimal frame in which blood vessels in the target region are captured with the contrast agent sufficiently filled therein, thus clearly distinguishing the blood vessel region and the other regions.

The information processing system may sequentially list the intensities for each of a plurality of frame images included in the medical image according to frame numbers (in order of time the images are captured), and obtain the distribution 610 of intensities for the frame images (e.g., a dot graph of intensities according to frame numbers). The information processing system may select a plurality of consecutive frame images having an intensity for the frame image within a predefined threshold range 630, and detect a frame section 640 corresponding to the selected plurality of consecutive frame images.

For example, in order to detect the frame section 640, the information processing system may approximate the distribution 610 of the intensities for the frame image with a continuous function. As a specific example, the information processing system may approximate the distribution 610 of intensities for the frame image with a polynomial function (e.g., a quadratic function), but aspects are not limited thereto, and it may be approximated with any function. The maximum value of the approximated continuous function 620 may be calculated. The threshold range 630 may be defined based on the calculated maximum value. In this example, the threshold range 630 may be defined in consideration of the intensity range of the entire medical image. As a specific example, the upper limit of the threshold range may be defined as the maximum value+0.1*(the difference between the maximum and minimum values of intensity for multiple frame images), and the lower limit of the threshold range may be defined as the maximum value−0.1*(the difference between the maximum and minimum intensity values for multiple frame images). The information processing system may select a plurality of consecutive frame images included in the defined threshold range 630, and detect the frame section 640 (e.g., a section from the 14th frame to the 25th frame) corresponding to the selected plurality of consecutive frame images.

Figure 7:
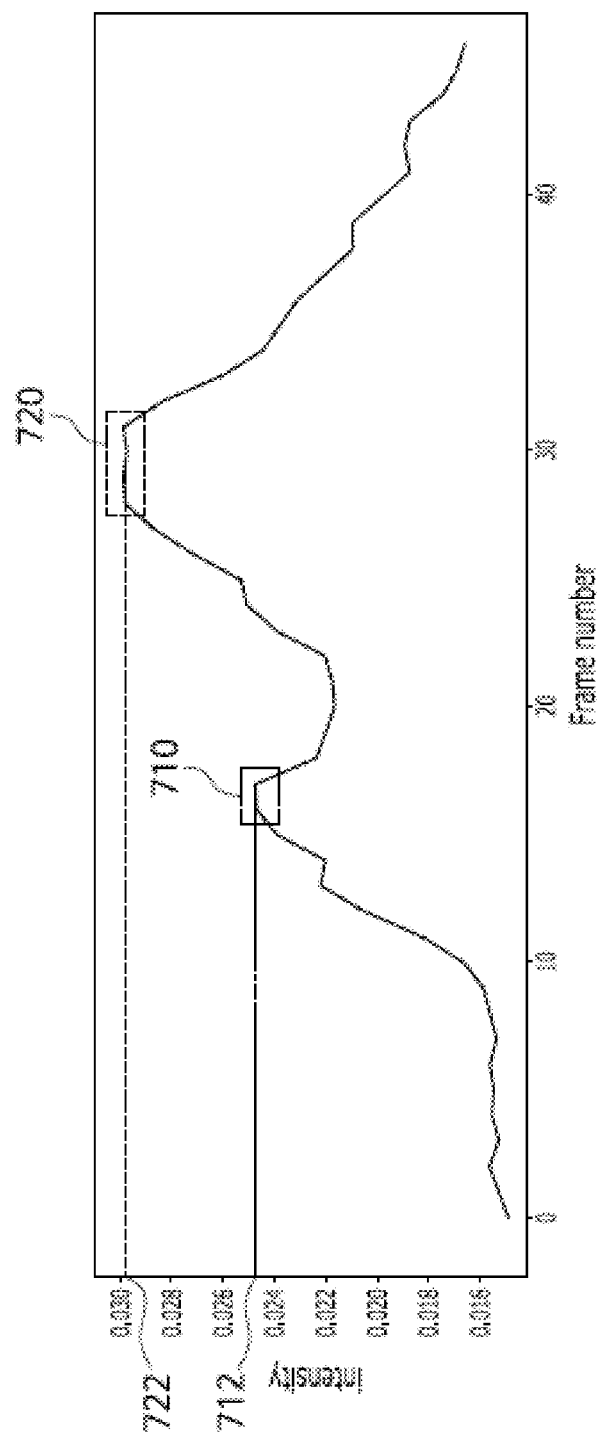
FIG. 7 is a diagram illustrating an example of a method for determining one final frame section from a plurality of detected frame sections.

FIG. 7 is a diagram illustrating an example of a method for determining one final frame section from a plurality of detected frame sections 710 and 720. The plurality of frame sections 710 and 720 may be detected in the process of detecting the frame section described above with reference to FIG. 6. For example, there may be several frame sections where the intensity for the frame image is continuously included within a predefined threshold range, in which case a plurality of frame sections may be detected. As another example, if a plurality of maximum values are calculated from the approximated continuous function, a plurality of threshold ranges may be defined, in which case a plurality of frame sections may be detected. In the example shown in FIG. 7, when examining the distribution of intensities for each frame image, it can be seen that two frame sections 710 and 720 are detected and two maximum values 712 and 722 are calculated, and accordingly, two threshold ranges are defined. As described above, it is possible that a plurality of frame sections are detected in the process of detecting the frame section, and in this case, the information processing system may determine, as the final frame section, one frame section of the plurality of detected frame sections 710 and 720.

The information processing system may determine, as the final frame section, a frame section having the largest maximum value 712 and 722 serving as a criterion for detecting a frame section. In the example shown, between the detected first frame section 710 and the second frame section 720, the second frame section 720 having the larger maximum value 722 as the criterion for the threshold range may be determined to be the final frame section. According to another example, the information processing system may determine a frame section to be the final frame section, if the frame section has the largest number of frame images corresponding to the frame section. In the example shown, the second frame section 720 having a greater number of frame images corresponding to the frame section may be determined to be the final frame section. According to another example, the information processing system may determine, as the final frame section, a frame section having one of the largest maximum intensity value, the largest minimum intensity value, or the largest average intensity for the frame image corresponding to the frame section. In the example shown, the second frame section 720 having a larger maximum intensity value, larger minimum intensity value, and larger average intensity for the frame image corresponding to the frame section than those of the first frame section 710 may be determined to be the final frame section. In addition, various other methods for determining a section having the stably maintained high intensity for the frame image from a plurality of detected sections may be applied.

Figure 8:
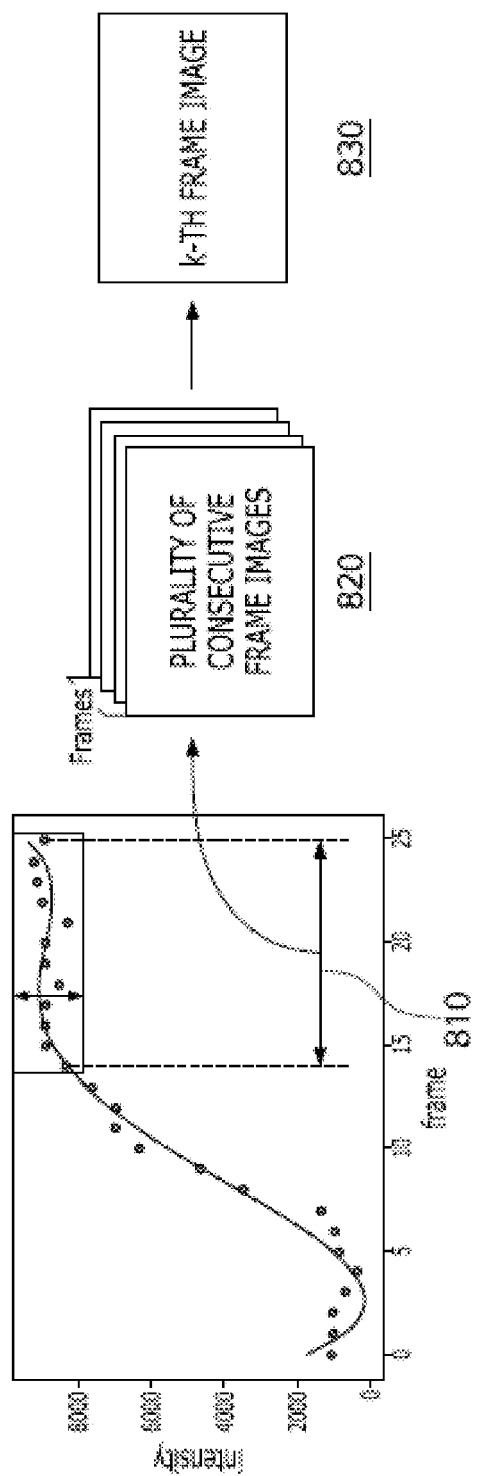
FIG. 8 is a diagram illustrating an example of a method for selecting an optimal frame from the determined frame section.

FIG. 8 is a diagram illustrating an example of a method for selecting an optimal frame 830 from a determined frame section 810. The information processing system may select one frame image from among a plurality of consecutive frame images 820 corresponding to the determined frame section 810 to select the optimal frame 830. For example, the information processing system may select a frame image having the highest intensity in the determined frame section 810 to be the optimal frame 830. As another example, the information processing system may select a frame image corresponding to the last frame of the frame section 810 to be the optimal frame 830. This is because the last frame of the frame section 810 having the stably maintained high intensities may be a frame captured with the contrast agent being most evenly and fully filled in the blood vessels of the target region. The intensities for the frame images captured after this frame may be rapidly reduced.

The information processing system may receive not only a medical image but also electrocardiogram (ECG) data of a patient, which may be measured at the same time as when the medical image is captured. In this case, the information processing system may use the electrocardiogram data to select the optimal frame 830. For example, the information processing system may select a frame corresponding to the end of diastole in the determined frame section 810 and extract a frame image corresponding to the selected frame, thereby selecting the optimal frame 830 in which a blood vessel region is clearly distinguished.

Figure 9:
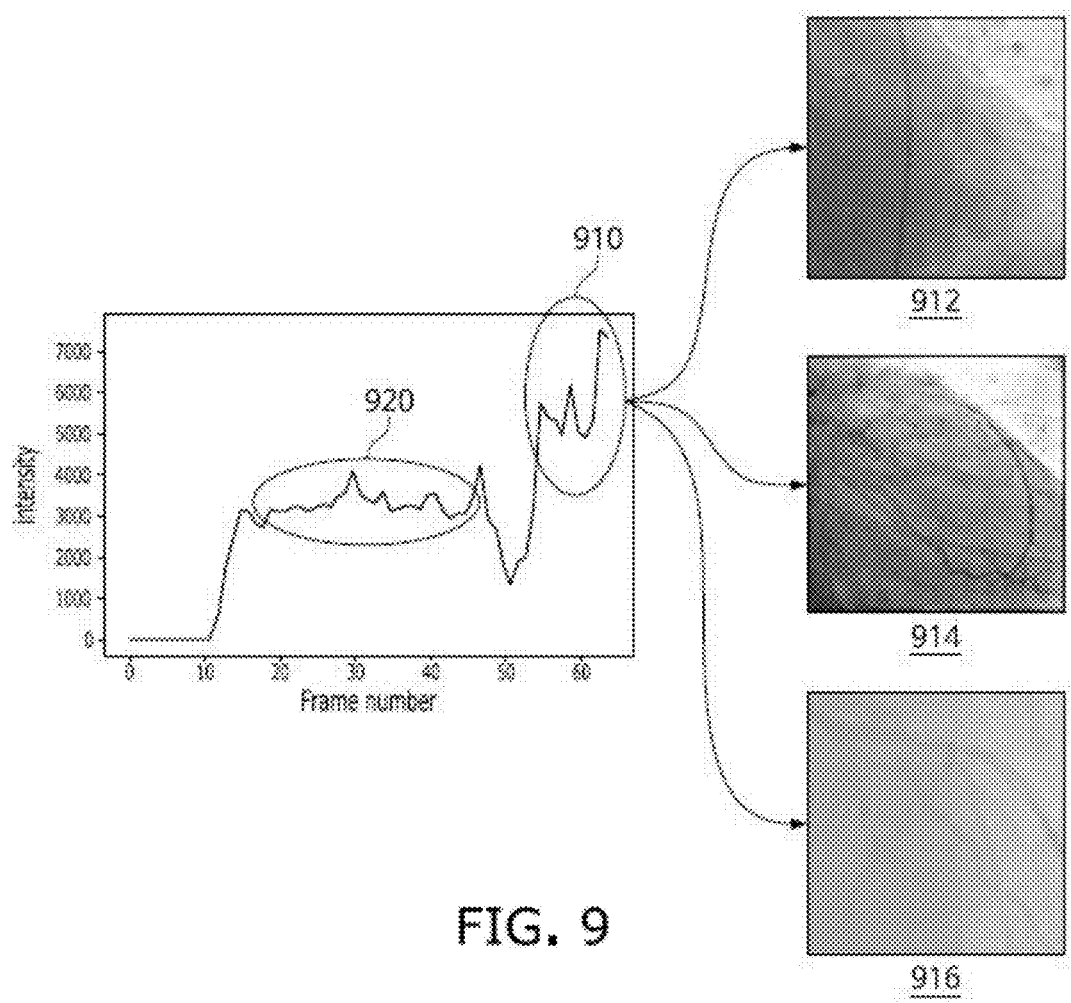
FIG. 9 is a diagram illustrating an example of an optimal frame presenting section selected according to a related method and an optimal frame presenting section selected according to an example of the present disclosure.

FIG. 9 is a diagram illustrating an example of an optimal frame presenting section 910 selected according to a related method and an optimal frame presenting section 920 selected according to an example. According to a related method for selecting an optimal frame from among a plurality of frame images included in the medical image, a frame image of the plurality of frame images that has the highest intensity of the contrast agent is selected as an optimal frame. According to this related method, the optimal frame presenting section 910 may be selected from a peak section where the intensity rapidly increases in the distribution of intensities for each frame image. The frame image present in this peak section may momentarily show a high intensity of contrast agent because a foreign material (e.g., catheter), not the contrast agent, is determined to be the intravascular contrast agent in a frame image 912 that is captured at the moment the foreign material is inserted, or because the frame image is a frame image 914 that is captured in a state that the contrast agent has flown out so that the contrast agent barely remains in certain vessel regions, and only some blood vessel regions are filled with the contrast agent, or because the frame image 914 is temporarily out of focus and not suitable for analysis, but converted into binary data (e.g., relatively dark regions are converted to contrast agent region (1), and relatively light regions are converted into surrounding regions (0)). That is, according to the related method, there may be an error of measuring a maximum intensity of contrast agent and selecting a corresponding frame to be the optimal frame, while the frame actually does not clearly distinguish the blood vessel and the surroundings in the image and not suitable for analysis.

On the other hand, according to the present disclosure, by determining the frame section 920 having the stably maintained intensity using the distribution of intensities for each frame image, and selecting an optimal frame from the determined frame section 920, it is possible to prevent an error of selecting a frame image not suitable for analysis as an optimal frame due to perturbation as described above, and accordingly, a frame image suitable for analysis can be selected.

Figure 10:
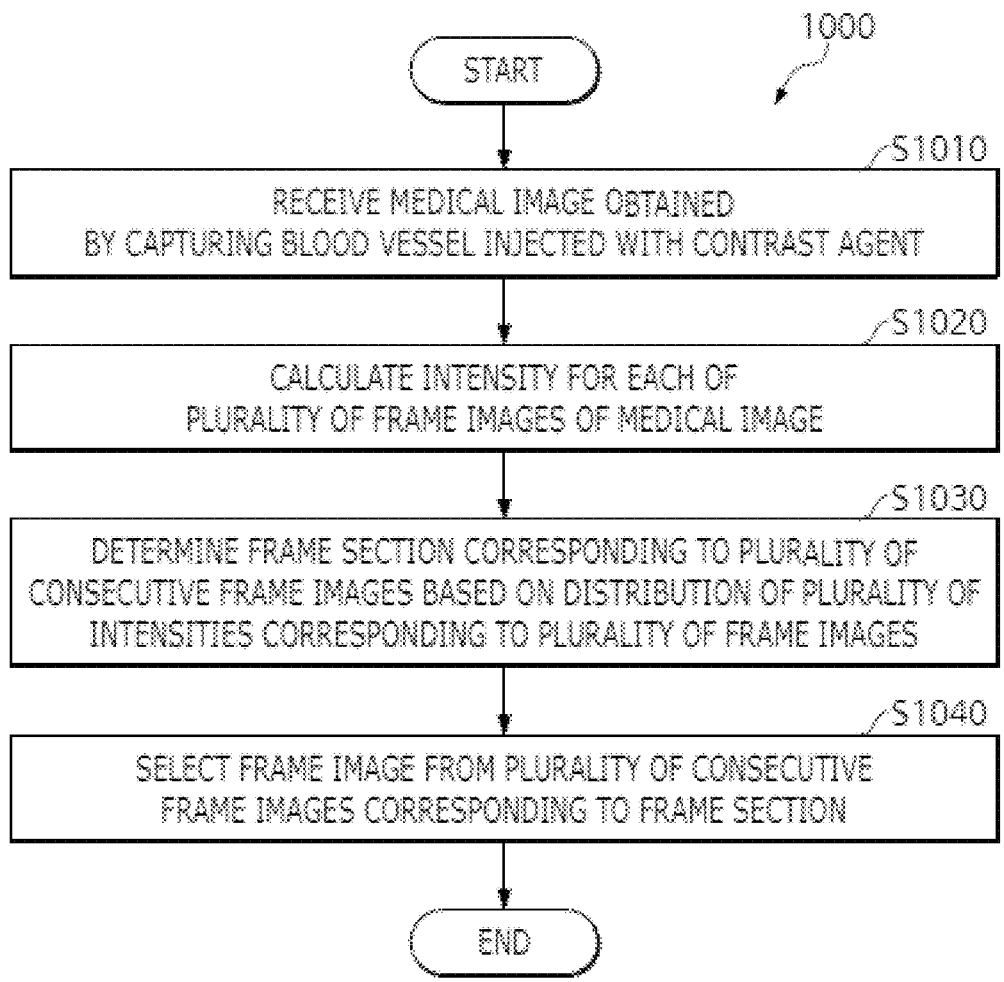
FIG. 10 is a flowchart illustrating an example of a method for selecting an optimal frame using a distribution of intensities for each frame image of a medical image.

FIG. 10 is a flowchart illustrating an example of a method 1000 for selecting an optimal frame using a distribution of intensities for each frame image of a medical image. The method 1000 may be initiated by a processor (e.g., one or more processors of an information processing system) receiving a medical image obtained by capturing a blood vessel administered a contrast agent, at S1010. In this case, the medical image may include a plurality of frame images.

The processor may calculate intensity for each of a plurality of frame images of the medical image, at S1020. In this case, the intensity for the frame image may refer to the intensity of the contrast agent which may be calculated from the frame image. For example, the intensity for the frame image may be a numerical value reflecting the degree that the region corresponding to the blood vessel filled with the contrast agent is distinguished from the rest of the region in the frame image. The intensity for the frame image may be calculated with various methods.

The processor may mask a region determined to be the blood vessel in each of a plurality of frame images of the medical image by using a machine learning model, and calculate the intensity for each of the frame images of the medical image based on the masked region. According to another example, the processor may calculate reliability values for each of a plurality of pixels in each of a plurality of frame images of the medical image is determined to be the blood vessel region, and calculate the intensity for each of the plurality of frame images of the medical image based on the calculated reliability values.

The processor may determine a frame section corresponding to a plurality of consecutive frame images based on the distribution of a plurality of intensities corresponding to a plurality of frame images, at S1030. The processor may determine a continuous frame section having stably maintained intensities with various methods.

The processor may select, from among a plurality of frame images of the medical image, a plurality of consecutive frame images having intensities for the frame images within a predefined threshold range, and detect a frame section corresponding to the selected plurality of consecutive frame images. For example, the processor may approximate the calculated intensity for each of the plurality of frame images with a continuous function, and calculate a maximum value of the approximated continuous function. The processor may select a plurality of consecutive frame images included in a threshold range defined based on the calculated maximum value and detect a frame section corresponding to the selected plurality of consecutive frame images.

Meanwhile, there may be several frame sections corresponding to a plurality of consecutive frame images having the intensity for the frame image included in the predefined threshold range, in which case a plurality of frame sections may be detected. In addition, if a plurality of maximum values are calculated from the approximated continuous function, a plurality of threshold ranges may be calculated, and thus a plurality of frame sections may be detected. Accordingly, a plurality of frame sections may be detected in the process of detecting the frame section, and in this case, the processor may determine one section from the detected sections. For example, the processor may determine a frame section to be the final frame section if the frame section has the largest maximum value that serves as a criterion for detecting the frame section. As another example, the processor may determine a frame section to be the final frame section if the frame section has the largest number of frame images corresponding to the frame section. As yet another example, the processor may determine a frame section to be the final frame section if the frame section has one of the largest maximum intensity value, the largest minimum intensity value, or the largest average intensity for the frame images corresponding to the frame section.

The processor may select one frame image from among a plurality of consecutive frame images corresponding to the determined frame section, at S1040. For example, the processor may select a frame image having the highest intensity in the frame section to be an optimal frame. As another example, a frame image corresponding to the last frame of the frame section may be selected to be an optimal frame. As yet another example, the processor may receive electrocardiogram data that was measured at the same time as when the medical image was captured, and in this case, in which case the processor may select a frame corresponding to the end of diastole within a frame section using the received electrocardiogram data and extract a frame image corresponding to the selected frame so as to select an optimal frame.

The flowchart shown in FIG. 10 and the above description are merely examples, and may be implemented in various ways. For example, one or more steps may be added or omitted, the order of each step may be changed, or at least some steps may be performed in parallel.

The method described above may be provided as a computer program stored in a computer-readable recording medium for execution on a computer. The medium may be a type of medium that continuously stores a program executable by a computer, or temporarily stores the program for execution or download. In addition, the medium may be a variety of recording means or storage means having a single piece of hardware or a combination of several pieces of hardware, and is not limited to a medium that is directly connected to any computer system, and accordingly, may be present on a network in a distributed manner. An example of the medium includes a medium configured to store program instructions, including a magnetic medium such as a hard disk, a floppy disk, and a magnetic tape, an optical medium such as a CD-ROM and a DVD, a magnetic-optical medium such as a floptical disk, and a ROM, a RAM, a flash memory, and so on. In addition, other examples of the medium may include an app store that distributes applications, a site that supplies or distributes various software, and a recording medium or a storage medium managed by a server.

The methods, operations, or techniques of the present disclosure may be implemented by various means. For example, these techniques may be implemented in hardware, firmware, software, or a combination thereof. Those skilled in the art will further appreciate that various illustrative logical blocks, modules, circuits, and algorithm steps described in connection with the disclosure herein may be implemented in electronic hardware, computer software, or combinations of both. To clearly illustrate this interchangeability of hardware and software, various illustrative components, blocks, modules, circuits, and steps have been described above generally in terms of their functionality. Whether such a function is implemented as hardware or software varies according to design requirements imposed on the particular application and the overall system. Those skilled in the art may implement the described functions in varying ways for each particular application, but such implementation should not be interpreted as causing a departure from the scope of the present disclosure.

In a hardware implementation, processing units used to perform the techniques may be implemented in one or more ASICs, DSPs, digital signal processing devices (DSPDs), programmable logic devices (PLDs), field programmable gate arrays (FPGAs), processors, controllers, microcontrollers, microprocessors, electronic devices, other electronic units designed to perform the functions described in the present disclosure, computer, or a combination thereof.

Accordingly, various example logic blocks, modules, and circuits described in connection with the present disclosure may be implemented or performed with general purpose processors, DSPs, ASICs, FPGAs or other programmable logic devices, discrete gate or transistor logic, discrete hardware components, or any combination of those designed to perform the functions described herein. The general purpose processor may be a microprocessor, but in the alternative, the processor may be any related processor, controller, microcontroller, or state machine. The processor may also be implemented as a combination of computing devices, for example, a DSP and microprocessor, a plurality of microprocessors, one or more microprocessors associated with a DSP core, or any other combination of the configurations.

In the implementation using firmware and/or software, the techniques may be implemented with instructions stored on a computer-readable medium, such as random access memory (RAM), read-only memory (ROM), non-volatile random access memory (NVRAM), programmable read-only memory (PROM), erasable programmable read-only memory (EPROM), electrically erasable PROM (EEPROM), flash memory, compact disc (CD), magnetic or optical data storage devices, and the like. The instructions may be executable by one or more processors, and may cause the processor(s) to perform certain aspects of the functions described in the present disclosure.

Although the examples described above have been described as utilizing aspects of the currently disclosed subject matter in one or more standalone computer systems, aspects are not limited thereto, and may be implemented in conjunction with any computing environment, such as a network or distributed computing environment. Furthermore, the aspects of the subject matter in the present disclosure may be implemented in multiple processing chips or devices, and storage may be similarly influenced across a plurality of devices. Such devices may include PCs, network servers, and portable devices.

Although the present disclosure has been described in connection with some examples herein, various modifications and changes can be made without departing from the scope of the present disclosure, which can be understood by those skilled in the art to which the present disclosure pertains. In addition, such modifications and changes should be considered within the scope of the claims appended herein.

The invention claimed is:

1. A method performed by a computing device, the method comprising:
receiving a medical image associated with a blood vessel injected with a contrast agent, wherein the medical image comprises a plurality of frame images;
calculating an intensity for each of the plurality of frame images of the medical image;
approximating the calculated intensity for each of the plurality of frame images with a continuous function;
calculating a local maximum value of the continuous function;
determining, based on a distribution of a plurality of intensities corresponding to the plurality of frame images, a frame section corresponding to a plurality of consecutive frame images of the plurality of frame images; and
selecting, based on the determined frame section, a frame image from among the plurality of consecutive frame images,
wherein the determining the frame section comprises:
selecting, from among the plurality of frame images of the medical image, a plurality of consecutive frame images having intensities within a predefined threshold range, wherein the predefined threshold range is defined based on the calculated local maximum value; and determining, as the frame section, a frame section corresponding to the selected plurality of consecutive frame images.

2. The method according to claim 1, wherein the calculating the intensity for each of the plurality of frame images of the medical image comprises:
   masking, using a machine learning model, a region determined to be the blood vessel in a first frame image of the plurality of frame images of the medical image; and
   calculating, based on the masked region, the intensity for the first frame image of the plurality of frame images of the medical image.

3. The method according to claim 1, wherein the calculating the intensity for each of the plurality of frame images of the medical image comprises:
   calculating a reliability value for determining each of a plurality of pixels in each of the plurality of frame images of the medical image to be a blood vessel region; and
   calculating, based on the calculated reliability value, the intensity for each of the plurality of frame images of the medical image.

4. The method according to claim 1, wherein the determining the frame section further comprise:
   as a criterion for determining the frame section, determining, based on a plurality of detected frame sections, a detected frame section having a largest local maximum value.

5. The method according to claim 4, wherein the largest local maximum value corresponds to a largest value among of a plurality of local maximum values of the continuous function.

6. The method according to claim 1, wherein the determining the frame section further comprises:
   based on a plurality of detected frame sections, determining, as the frame section, a detected frame section having a largest number of frame images, or a detected frame section having one of a largest maximum intensity value, a largest minimum intensity value, or a largest average intensity for frame images.

7. The method according to claim 1, wherein the selecting the frame image comprises selecting, as the frame image, a frame image having a highest intensity in the frame section or a last frame image in the frame section.

8. The method according to claim 1, further comprising:
   receiving electrocardiogram data measured when the medical image is captured,
   wherein the selecting the frame image comprises
      selecting a frame image corresponding to an end of diastole in the frame section using the electrocardiogram data.

9. The method according to claim 1, wherein the selected frame image comprises:
   a first region corresponding to the blood vessel; and
   a second region distinguishable from the first region.

10. An information processing system, comprising:
    one or more processors; and
    a memory storing instructions that, when executed by the one or more processors, cause the information processing system to:
       receive a medical image associated with a blood vessel injected with a contrast agent, wherein the medical image comprises a plurality of frame images;
       calculate an intensity for each of the plurality of frame images of the medical image;
       approximate the calculated intensity for each of the plurality of frame images with a continuous function;
       calculate a local maximum value of the continuous function;
       determine, based on a distribution of a plurality of intensities corresponding to the plurality of frame images, a frame section corresponding to a plurality of consecutive frame images of the plurality of frame images; and
       select, based on the determined frame section, a frame image from among the plurality of consecutive frame images,
    wherein the determining the frame section comprises:
       selecting, from among the plurality of frame images of the medical image, a plurality of consecutive frame images having intensities within a predefined threshold range, wherein the predefined threshold range is defined based on the calculated local maximum value; and
       determining, as the frame section, a frame section corresponding to the selected plurality of consecutive frame images.

11. The information processing system according to claim 10, wherein the instructions, when executed by the one or more processors, cause the information processing system to determine the frame section by:
    as a criterion for determining the frame section, determining, based on a plurality of detected frame sections, a detected frame section having a largest local maximum value.

12. The information processing system according to claim 11, wherein the largest local maximum value corresponds to a largest value among of a plurality of local maximum values of the continuous function.

* * * * *